(12) United States Patent
Beeler et al.

(10) Patent No.: US 10,329,627 B1
(45) Date of Patent: Jun. 25, 2019

(54) METHOD FOR PREDICTING AND MONITORING RESPONSE TO AN IMMUNE CHECKPOINT INHIBITOR

(71) Applicant: Inivata Ltd., Cambridge (GB)

(72) Inventors: John Beeler, Melrose, MA (US);
Vincent Plagnol, Cambridge (GB);
Greg Jones, Morrisville, NC (US)

(73) Assignee: INIVATA LTD., Cambridge (GB)

( * ) Notice: Subject to any disclaimer, the term of this patent is extended or adjusted under 35 U.S.C. 154(b) by 0 days.

(21) Appl. No.: 16/013,869

(22) Filed: Jun. 20, 2018

Related U.S. Application Data (60) Provisional application No. 62/661,554, filed on Apr. 23, 2018, provisional application No. 62/670,525, filed on May 11, 2018, provisional application No. 62/675,655, filed on May 23, 2018, provisional application No. 62/682,052, filed on Jun. 7, 2018.

(51) Int. Cl.
| | |
|---|---|
| C07H 21/04 | (2006.01) |
| C12Q 1/68 | (2018.01) |
| C12Q 1/6886 | (2018.01) |
| A61K 39/395 | (2006.01) |
| C07K 16/28 | (2006.01) |
| A61P 35/00 | (2006.01) |
| C12Q 1/6806 | (2018.01) |

(52) U.S. Cl.
CPC ........ *C12Q 1/6886* (2013.01); *A61K 39/3955* (2013.01); *A61P 35/00* (2018.01); *C07K 16/2818* (2013.01); *C07K 16/2827* (2013.01); *C12Q 1/6806* (2013.01)

(58) Field of Classification Search
None
See application file for complete search history.

(56) References Cited

PUBLICATIONS

Khoo et al. (Transl Lung Cancer Research, vol. 4, No. 2, pp. 126-141, 2015) (Year: 2015).*
Chen et al. (Scientific Reports, vol. 6, pp. 1-8, 2016) (Year: 2016).*
Dong et al. (Clinical Cancer Research, vol. 23, No. 12, pp. 3012-3024, Jun. 15, 2017) (Year: 2017).*
Beavis et al.,"CD73: A potential biomarker for anti-PD-1 therapy", OncoImmunology; Nov. 2015; 4:11, total 3 pages.

(Continued)

*Primary Examiner* — Jeanine A Goldberg
(74) *Attorney, Agent, or Firm* — James S. Keddie; Bozicevic, Field & Francis (57) ABSTRACT

A method for analyzing cell free DNA (cfDNA) from the bloodstream of a cancer patient is provided. In some embodiments, the method may comprise sequencing at least part of the coding sequences of TP53 and KRAS in a sample of the cfDNA, analyzing the sequences to identify nucleotide transversions in the coding sequences of the genes, relative to reference sequences of the genes. In some embodiments, the method may comprise counting the total number of identified nucleotide transversions. The presence of nucleotide transversions indicates that the patient will be more responsive to the immune checkpoint inhibitor, whereas a decreased number of transversions or no transversions indicates that the patient will be less responsive to the immune checkpoint inhibitor.

11 Claims, 5 Drawing Sheets

(56) References Cited

PUBLICATIONS

Cesano et al., "Bringing the Next Generation of Immuno-Oncology Biomarkers to the Clinic", Biomedicines.; Feb. 2, 2018; 6, 14, total 11 pages.

Christiaens et al., "The challenge of RNAi-mediated control of hemipterans", Current Opinion in Insect Science 2014, 6:15-21.

Dong et al., "Potential Predictive Value of TP53 and KRAS Mutation Status for Response to PD-1 Blockade Immunotherapy in Lung Adenocarcinoma", Clin Cancer Res. Jun. 15, 2017; 23(12):3012-3024.

Gainor et al., "EGFR Mutations and ALK Rearrangements Are Associated with Low Response Rate to PD-1 Pathway Blockade in Non-Small Cell Lung Cancer (NSCLC): A Retrospective Analysis", Author Manuscript May 25, 2016, total 31 pages.

Goodman et al., "Tumor Mutational Burden as an Independent Predictor of Response to Immunotherapy in Diverse Cancers", Molecular Cancer Therapeutics. Nov. 2017; 16(11):2598-2608.

Goswami et al., "A Potential biomarker for anti-PD-1 immunotherapy", Nature Medicine; Feb. 2018; 24:123-124.

Grigg et al., "PD-L1 biomarker testing for non-small cell lung cancer: truth or fiction?" ImmunoTherapy of Cancer (2016); 4:48, total 10 pages.

Hellmann et al., "Genomic Features of Response to Combination Immunotherapy in Patients with Advanced Non-Small-Cell Lung Cancer", Cancer Cell. May 14, 2018; 33(5):843-852.

Herbst et al. "Predictive correlates of response to the anti-PD-L1 antibody MPDL3280A in cancer patients", Nature. Nov. 27, 2014; 515(7528):563-567.

Kim et al., "Prognostic value of KRAS mutation in advanced non-small-cell lung cancer treated with immune checkpoint inhibitors: A meta-analysis and review", Oncotarget, May 3, 2017 ; 8(29):48248-48252.

Onyshchenko, "The Puzzle of Predicting Response to Immune Checkpoint Blockade", EBiomedicine, Jun. 19, 2018, total 2 pages.

Vareki et al., "Biomarkers of Response to PD-1/PD-L1 inhibition", Critical Reviews in Oncology/Hematology, Aug. 2017 ; 116:116-124.

Chaudhuri et al., "Early Detection of Molecular Residual Disease in Localized Lung Cancer by Circulating Tumor DNA Profiling", Cancer Discovery, 2017, pp. 1394-1403.

George et al., "Loss of PTEN Is Associated with Resistance to Anti-PD-1 Checkpoint Blockade Therapy in Metastatic Uterine Leiomyosarcoma", Immunity Report, 2017, 46(2): 197-204.

Hong et al., "Kras, Egfr, and Tp53 Mutations in B6C3F1/N Mouse and F344/NTac Rat Alveolar/Bronchiolar Carcinomas Resulting from Chronic Inhalation Exposure to Cobalt Metal", Toxicologic Pathology, 2015, 43: 872-882.

Koyama et al., "STK11/LKB1 Deficiency Promotes Neutrophil Recruitment and Proinflammatory Cytokine Production to Suppress T-cell Activity in the Lung Tumor Microenvironment", Cancer Research, 2016, 76(5): 999-1008.

Lea et al., "Genetic pathways and mutation profiles of human cancers: site- and exposure-specific patterns", Carcinogenesis, 2007, 28(9): 1851-1858.

Peng et al., "Loss of PTEN Promotes Resistance to T Cell Mediated Immunotherapy", Cancer Discovery, 2015, 6(2): 202-216.

Rizvi et al., "Mutational landscape determines sensitivity to PD-1 blockade in non-small cell lung cancer", Science, 2015, 348(6230): 124-128.

Rizvi et al., "Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing", Journal of Clinical Oncology, 2018, 36(7): 633-641.

Scoccianti et al., "Prognostic value of TP53, KRAS and EGFR mutations in nonsmall cell lung cancer: the EUELC cohort", Eur Respir J., 2012, 40: 177-184.

Villaflor et al., "Biopsy-free circulating tumor DNA assay identifies actionable mutations in lung cancer", Oncotarget, 2016, 7(41): 66880-66891.

Yang et al., "Circulating mutational portrait of cancer: manifestation of aggressive clonal events in both early and late stages", Journal of Hematology & Oncology, 2017, 10:100.

\* cited by examiner

FIG. 1

| patientID | Timepoint | Mutations detected | Genomic Alteration | Transversion (Tv) Transition (Ts) | Gene name | Protein change | Consequence | Cosmic name | Allele Frequency | Clinical Response |
|---|---|---|---|---|---|---|---|---|---|---|
| 204 | Baseline prior to cycle 1 Atezolimumab | Yes | mis_chr17_7670709_C_A | Tv | TP53 | p.G334W | missense_variant | COSM48816 | 5.9125 | Partial Response |
|  |  |  | mis_chr17_7674921_C_A | Tv | TP53 | p.E204* | stop_gained | COSM10804 | 7.1625 |  |
| 206 | Baseline prior to cycle 1 Nivolumab | Yes | mis_chr12_25245350_C_G | Tv | KRAS | p.G12A | missense_variant | COSM522 | 0.12766 | Partial Response |
| 210 | Baseline prior to cycle 1 Atezolimumab | Yes | mis_chr17_7674953_T_A | Ts | TP53 | p.H193L | missense_variant | COSM2744772 | 0.875 | Progressive Disease |
|  |  |  | del_chr19_12220484_CTCCGACCTGG_- | NA | STK11 | p.192-196:iSDLG/frameshift_variant |  | NA | 1.55385 |  |
| 219 | Baseline prior to cycle 1 Nivolumab | Yes | mis_chr12_25245347_C_T | Tv | KRAS | p.G13D | missense_variant | COSM532 | 3.02308 | Progressive Disease |

METHOD FOR PREDICTING AND MONITORING RESPONSE TO AN IMMUNE CHECKPOINT INHIBITOR

CROSS-REFERENCE TO RELATED APPLICATIONS

This application claims the benefit of U.S. Application Ser. No. 62/661,554, filed on Apr. 23, 2018, U.S. Application Ser. No. 62/670,525, filed on May 11, 2018, U.S. Application Ser. No. 62/675,655, filed on May 23, 2018, and U.S. Application Ser. No. 62/682,052, filed on Jun. 7, 2018, all of which applications are incorporated by reference herein.

BACKGROUND

The landscape of oncology drug development is rapidly changing with the introduction of immune-targeting therapies. Specifically, recent approvals of monoclonal antibodies that target Programmed Death Receptor (PD-1), Programmed Death Ligand 1 (PD-L1) and other immune checkpoints have demonstrated durable clinical benefit across a range of tumor indications. Unfortunately, clinical benefit is limited to a small fraction of patients highlighting the urgent need for predictive biomarkers capable of identifying patients most likely to benefit and prevent needless exposure to therapies with associated high costs and potential of adverse autoimmune effects.

Currently, the overexpression of PD-L1 has been identified as a predictive biomarker for the response to PD-1/PD-L1 targeting antibodies. However, detection of PD-L1 expression by IHC is a controversial predictive biomarker of which patients may benefit from therapy. Several factors have been attributed to why PD-L1 immunohistochemical (IHC) staining is limited in its predictive ability. For example, IHC detection methods are sometimes unreliable. PD-L1 expression is determined using an anti-PD-L1 antibody by IHC staining of formalin-fixed paraffin-embedded tumor tissue. Staining is confounded by variable technical factors including pre-analytical factors (proper tissue collection, handling, preservation & storage); analytical factors (tissue section thickness, tumor content, staining on non-tumor cells; spatial & temporal limitations of the tissue) and post-analytical factors (operation bias in assessing staining intensity; lack of harmonization in procedures and cut-offs with the 5 available PD-L1 companion diagnostic IHC assays). In addition, there is both intra and inter-patient heterogeneity of PD-L1 expression within a given specimen as well as between the primary and metastatic lesion. Finally, PD-L1 expression is dynamic and can be induced by activated antigen-specific T cells, therapeutics and cytokines within the tumor microenvironment illustrating that evaluation of a single time point may not be reflective of the current responsive state of a tumor to PD-1/PD-L1 targeting therapy.

Recently, tumor mutational burden (TMB) (i.e., the total number of mutations per coding area of a tumor genome) has emerged as a biomarker of response to anti-PD-1 therapy. Using whole-exome sequencing of non-small cell lung cancers treated with pembrolizumab, higher nonsynonymous mutation burden in tumors was associated with improved objective response, durable clinical benefit, and progression-free survival. However, despite the promise of TMB, there are reported cases where patients with high TMB fail to respond to PD-1/PD-L1 targeting therapy as well as patients with low TMB responding to check point inhibitor therapy. Other methods, including non-invasive methods, for predicting response to immune checkpoint inhibitors such as anti-PD-1 or anti-PD-L1 antibodies are therefore needed.

SUMMARY

Some embodiments of the present method are based, at least in part, on the discovery that a cancer patient's response to one or more immune checkpoint inhibitors such as an anti-PD-1 or anti-PD-L1 antibody can be reliably predicted by whether nucleotide transversions are found in a relatively small number of coding sequences, e.g., the coding sequences of TP53 and KRAS, and optionally, the coding sequences of CDKN2A and NFE2L2, in cell free DNA obtained from the bloodstream of the patient. An increased number of nucleotide transversions in these genes indicates that the patient will be more responsive to the immune checkpoint inhibitor, whereas a decreased number of transversions or no transversions in these genes indicates that the patient will be less responsive to the immune checkpoint inhibitor.

In some embodiments, the method may involve analyzing cell free DNA (cfDNA) from the bloodstream of a cancer patient. In these embodiments, the method may comprise sequencing at least part of the coding sequences of TP53 and KRAS (e.g., the coding sequences of TP53, KRAS, CDKN2A and NFE2L2) in a sample of the cfDNA, and analyzing the sequences to identify nucleotide transversions in the coding sequences of the genes, relative to reference sequences of those genes. In some embodiments, the method may comprise counting the total number of identified nucleotide transversions.

In some embodiments, the method may further comprise sequencing at least part of the coding sequences of PTEN and STK11 in the sample of cfDNA and analyzing those sequences to determine if there are any loss of function mutations in those genes. A loss of function mutation in either of those genes indicates that the patient will be less responsive or unresponsive to the immune checkpoint inhibitor.

In some embodiments, the method may further comprise sequencing at least part of the coding sequences of EGFR and BRAF in the sample of cfDNA to determine if there are any activating mutations in those genes. An activating mutation in either of those genes indicates that the patient will be less responsive or unresponsive to the immune checkpoint inhibitor.

In some embodiments, the method may further comprise determining whether there are any rearrangements in ALK and ROS1 in the sample of cfDNA. An ALK rearrangement or ROS1 rearrangement that results in a fusion indicates that the patient will be less responsive or unresponsive to the immune checkpoint inhibitor.

In some embodiments, the method may comprise providing a report indicating that there are nucleotide transversions in the genes analyzed and, optionally, whether there are any loss of function mutations in PTEN or STK11, whether there are any activating mutations in EGFR or BRAF and/or whether there are any rearrangements in ALK or ROS1. This report may be forwarded to a third party (e.g., a clinician) at a remote location in order to assist them in making a decision on which therapy a patient should be treated with. The method may be most effective on patients that have non-small cell lung cancer (NSCLC), although the method may be effective on patients that have other cancers, e.g., breast cancer etc. In some embodiments, the report may provide a "score" that indicates the likelihood that a patient will be responsive to therapy by an immune checkpoint inhibitor such as an anti-PD-1 or anti-PD-L1 antibody, where the score is based on the analysis summarized above and described below. The report may also provide treatment options.

A method for treating cancer is also provided. In some embodiments, this method may comprise: determining, in a sample of cfDNA from a cancer patient: (i) whether there are one or more nucleotide transversions in the coding sequences of at least TP53 and KRAS; (ii) whether there are any loss of function mutations in PTEN and STK11, (iii), whether there are any activating mutations in EGFR and BRAF and/or (iv) whether there are any rearrangements in ALK and ROS1, or receiving a report indicating the same; and identifying the patient as a candidate for treatment with an immune checkpoint inhibitor if the patient has one or more nucleotide transversions in the coding sequences of the TP53 and KRAS, no predicted loss of function mutations in PTEN and STK11, no activating mutations in EGFR and BRAF and no rearrangements in ALK and ROS1.

A method for monitoring treatment of a cancer that has been treated with an immune checkpoint inhibitor is also provided. In some embodiments, this method may comprise: (a) determining the allele frequency of one or more nucleotide transversions in the coding sequences of at least TP53 and KRAS in a sample of cfDNA from a cancer patient at a first time point, or receiving a report indicating the same, (b) determining the allele frequency of the one or more nucleotide transversions in the coding sequences of at least TP53 and KRAS in a sample of cfDNA from the cancer patient at a second time point, or receiving a report indicating the same; and (c) comparing the allele frequency of the one or more nucleotide transversions at the first time point to the allele frequency of the one or more nucleotide transversions at the second time point, thereby monitoring the treatment of the cancer.

In some embodiments, the method may comprise treating a patient with an immune checkpoint inhibitor, wherein the patient is suffering from cancer, the method comprising: (a) obtaining or having obtained a sample of blood from the patient; (b) performing or having performed a sequencing assay on cell-free DNA (cfDNA) from the sample to determine if the cell-free DNA comprises one or more nucleotide transversions in the coding sequences of TP53 and KRAS, relative to reference sequences of the TP53 and KRAS; and (c) if the patient has one or more nucleotide transversions in the coding sequences of the TP53 or KRAS, then administering an effective amount of the immune checkpoint inhibitor to the patient. In these embodiments, the sequencing assay may further determine if the cell-free DNA may comprise determining if there are one or more nucleotide transversions in the coding sequences of CDKN2A and NFE2L2.

In some embodiments, the method may comprise (a) obtaining or having obtained a sample of blood from the patient; (b) performing or having performed a sequencing assay on cell-free DNA (cfDNA) from the sample to determine if the cell-free DNA comprises: i. nucleotide transversions in the coding sequences of TP53 and KRAS, relative to reference sequences of TP53 and KRAS, and ii. predicted loss of function mutations in PTEN and STK11, iii. activating mutations in EGFR and BRAF, and iv rearrangements in ALK and ROS1; and (c) if the patient has one or more nucleotide transversions in the coding sequences of TP53 and KRAS, no predicted loss of function mutations in PTEN and STK11, no activating mutations in EGFR and BRAF and no rearrangements in ALK and ROS1, then administering an effective amount of the immune checkpoint inhibitor to the patient.

In any embodiment, the sequencing assay may comprise: sequencing at least part of the coding sequences of TP53, KRAS, and, optionally, CDKN2A and NFE2L2 in the sample of cfDNA and analyzing the sequences to determine if there are any transversions in TP53, KRAS, and, optionally, CDKN2A and NFE2L2, sequencing at least part of the coding sequences of PTEN and STK11 in the sample of cfDNA and analyzing the sequences to determine if there are any loss of function mutations in PTEN and STK11, sequencing at least part of the coding sequences of EGFR and BRAF in the sample of cfDNA and analyzing the sequences to determine if there are any activating mutations in EGFR or BRAF; and sequencing at least part of ALK and ROS1 in the sample of cfDNA and analyzing the sequences to determine if there are any rearrangements in ALK and ROS1, in the sample of cfDNA.

In any embodiment, the patient may have non-small cell lung cancer (NSCLC).

In all embodiments, the genes referenced in the determining steps are meant to be collective in the sense that if the method determines if there are one or more nucleotide transversions in the coding sequences of TP53 and KRAS, then the sequences of both TP53 and KRAS are analyzed and, if either or both of those genes contain a nucleotide transversion then the one or more nucleotide transversions are identified in TP53 and KRAS. In other words, in order for there to be one or more nucleotide transversions in TP53 and KRAS, a nucleotide transversion can be found in one gene, the other gene, or both genes. This wording is not meant to be interpreted as requiring that a nucleotide transversion must be found in both genes. Likewise, there is a predicted loss of function mutation in PTEN and STK11 if either or both of those genes contains a predicted loss of function mutation; there is an activating mutation in EGFR and BRAF if either or both of these genes contain an activating mutation, and there is a rearrangement in ALK and ROS1 if either of those genes has been rearranged.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

FIG. 1 is a flow chart illustrating an exemplary implementation of the method. In this flow chart, Y=Yes, N=No, NR indicates a patient that is predicted to not respond to immune checkpoint inhibition (i.e., a non-responder). These patients can be classified as having a "Low" score. R indicates a patient that is predicted to respond to immune checkpoint inhibition (i.e., a responder). These patients can be classified as having a "High" score. As would be apparent, the steps of this method could be performed in a different order or with different components.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing", as used herein, refer to the so-called parallelized sequencing-by-synthesis or sequencing-by-ligation platforms currently employed by Illumina, Life Technologies, and Roche, etc. Next-generation sequencing methods may also include nanopore sequencing methods such as that commercialized by Oxford Nanopore Technologies, electronic-detection based methods such as Ion Torrent technology commercialized by Life Technologies, or single-molecule fluorescence-based methods such as that commercialized by Pacific Biosciences.

The term "sequencing at least part of the coding sequences" refers sequencing at least 20% of, at least 40% of, at least 60% of, at least 80% of, or at least 90% of (e.g., all of), of the coding sequences.

The term "reference sequence", as used herein, refers to a known nucleotide sequence, e.g. a chromosomal region whose sequence is deposited at NCBI's Genbank database or other databases, for example. A reference sequence can be a wild type sequence.

As used herein, the terms "cell-free DNA from the bloodstream" and "circulating cell-free DNA" refers to DNA that is circulating in the peripheral blood of a patient. The DNA molecules in cell-free DNA may have a median size that is below 1 kb (e.g., in the range of 50 bp to 500 bp, 80 bp to 400 bp, or 100-1,000 bp), although fragments having a median size outside of this range may be present. Cell-free DNA may contain circulating tumor DNA (ctDNA), i.e., tumor DNA circulating freely in the blood of a cancer patient or circulating fetal DNA (if the subject is a pregnant female). cfDNA can be obtained by centrifuging whole blood to remove all cells, and then isolating the DNA from the remaining plasma or serum. Such methods are well known (see, e.g., Lo et al, Am J Hum Genet 1998; 62:768-75). Circulating cell-free DNA can be double-stranded or single-stranded.

As used herein, the term "circulating tumor DNA" (or "ctDNA") is tumor-derived DNA that is circulating in the peripheral blood of a patient. ctDNA is of tumor origin and originates directly from the tumor or from circulating tumor cells (CTCs), which are viable, intact tumor cells that shed from primary tumors and enter the bloodstream or lymphatic system. The precise mechanism of ctDNA release is unclear, although it is postulated involve apoptosis and necrosis from dying cells, or active release from viable tumor cells. ctDNA can be highly fragmented and in some cases can have a mean fragment size about 100-250 bp, e.g., 150 to 200 bp long. The amount of ctDNA in a sample of circulating cell-free DNA isolated from a cancer patent varies greatly: typical samples contain less than 10% ctDNA, although many samples have less than 1% ctDNA and some samples have over 10% ctDNA. Molecules of ctDNA can be often be identified because it contains tumorigenic mutations.

As used herein, the term "nucleotide transversion" refers to the substitution of a purine nucleotide (e.g., an A or G) with a pyrimidine nucleotide (e.g., a T or C), or substitution of a pyrimidine nucleotide (e.g., a T or C) with a purine nucleotide (e.g., an A or G). Nucleotide transversions include A to T, T to A, A to C, C to A, G to T, T to G, G to C and C to G transversions.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

A method for analyzing cell free DNA (cfDNA) from the bloodstream of a cancer patient is provided. As noted above, the method may comprise sequencing at least part of the coding sequences of TP53 and KRAS (and potentially other genes such as PTEN, STK11, EGFR, BRAF, CDKN2A, NFE2L2) and, optionally, as well as at least part of ALK and ROS1 in a sample of the cfDNA. Methods for sequencing target sequences in cfDNA are known and, in some embodiments, the method may comprise enriching for or amplifying target sequences by PCR prior to sequencing (see, e.g., Forshew et al, Sci. Transl. Med. 2012 4:136ra68, Gale et al, PLoS One 2018 13:e0194630 and Weaver et al, Nat. Genet. 2014 46:837-843, among many others). ALK and ROS1 fusions may be identified using similar methods, e.g., using PCR and the sequencing the products. These method may make use of primer pairs in which one primer hybridizes to the ALK or ROS1 gene and another primer hybridizes to a gene encoding a potential fusion partner for ALK or ROS1. In some embodiments, the method does not involve shotgun sequencing an unenriched/unamplified sample, or sequencing the entire exome. Rather, the sequencing may be done as part of a larger sequencing effort that targets at least part of the coding sequences for up to 200, e.g., up to 100 or up to 50 genes, focusing on the coding sequences of TP53 and KRAS (and potentially other genes such as PTEN, STK11, EGFR, BRAF, CDKN2A, NFE2L2) as well as others).

After the sequences have undergone initial processing, the sequences are analyzed to identify nucleotide transversions. This may be done by comparing the test sequence to a reference sequence, for each sequence being analyzed, and the identifying positions that contain a purine to pyrimidine substitution or pyrimidine to purine substitution. In some cases, this may comprise calling mutations de novo (e.g., using the method described by Forshew, supra, or another suitable method) and then determining which of those mutations are nucleotide transversions (as opposed to nucleotide transitions). Calling sequence variations in cell-free DNA can be challenging because the variant sequences are generally in the minority (e.g., less than 10% of the sequence). As such, if an amplicon sequencing strategy is employed, the method may comprise: (a) for each nucleotide position of a particular amplicon, determining, e.g., plotting, an error distribution that shows how often amplification and/or sequencing errors occur at different sequencing depths; (b) based on the distribution for each position of the sequence, determining a threshold frequency for each different sequencing depth at or above which a true genetic variation can be detected; (c) sequencing the sample to obtain plurality of reads for an amplicon; and determining, for each position of the amplicon, whether the frequency of a potential sequence variation in the sequence reads is above or below the threshold. Mutation may be identified (or "called") at a position if the frequency of sequence reads that contain the variation is above the threshold. In some cases, a substitution may be identified only if it occurs in the same amplicon from multiple independent amplification reactions. As would be apparent, if the sequencing is done using an amplicon approach, the method may comprise amplifying the coding sequences of the genes in a multiplex PCR reaction in which at least 10 amplicons (e.g., more than 10 and less than 50,000 amplicons, more than 10 and less than 10,000, more than 10 and less than 5,000 amplicons, more than 10 and less than 1,000 amplicons or more than 10 and less than 500 amplicons) or more than 10 and less than 100 amplicons are amplified (in duplicate, triplicate or quadruplicate, for example) and sequencing the amplicons. More or less amplicons can also be sequenced, if needed. In some embodiments, the primers used for amplification may not be completely specific for a single sequence, which can allow several hundred or several thousand amplicons to be consistently amplified in a single reaction. The amplicons sequenced can be of any suitable length and may vary in length. In some embodiments, the length of each amplicon, independently, may be in the range of 50 bp to 500 bp, although longer or shorter amplicons may be used in some implementations.

Next, the nucleotide transversions are identified and, in some embodiments, counted. The presence of nucleotide transversions in the coding sequences of TP53 and KRAS (and, optionally, CDKN2A and NFE2L2) in cfDNA correlates with the patient's response to immune checkpoint inhibition (e.g., PD-1 or PD-L1 blockade) and, as such, the presence of nucleotide transversions (or a score representing the same) in at least part of the coding sequences of TP53 and KRAS can be used to predict whether the patient will be susceptible to immune checkpoint inhibition. Identifying nucleotide transversions may comprise identifying A to C transversions, identifying C to A transversions, identifying G to T transversions, identifying T to G transversions, identifying A to T transversions, identifying T to A transversions, identifying G to C transversions and identifying C to G transversions. In some embodiments, the total number of nucleotide transversions may be counted.

In some embodiments, the method may comprise sequencing at least part of the coding sequences of TP53, KRAS, CDKN2A and NFE2L2 in the sample of cfDNA, and determining whether there are any nucleotide transversions in the coding sequences of those genes.

In some embodiments, the transversions may be identified de novo, i.e., without any expectation that they occur at a particular position or positions.

In some embodiments, the method may further comprise sequencing at least part of the coding sequences of PTEN and STK11 (also known as liver kinase B1 (LKB1) and renal carcinoma antigen NY-REN-19) in the sample of cfDNA, and analyzing the sequences to determine if there are any loss of function mutations in the genes. Examples of loss of function mutations include, but are not limited to mutations that generate a stop codon, mutations at splice junctions, and mutations that substitute a critical amino acid for another. The proteins encoded by these genes are well characterized (see, e.g., Worby et al, Annu. Rev. Biochem. 2014 83:641-69 and Zeqiraj et al, Science 2009 326: 1707-11), and they belong to well characterized families. As such, it should be relatively straightforward identify important or critical residues in those proteins. The presence of a loss of function mutation in either of these genes indicates that the patient would not be responsive to immune checkpoint blockade. As such, if there are no predicted loss of function mutations in PTEN or STK11, then the patient should be susceptible to immune checkpoint inhibition.

In some embodiments, the method may further comprise sequencing at least part of the coding sequences of EGFR and BRAF and determining whether there are any rearrangements in ALK and ROS1 that would result in the production of a fusion protein. In subsets of patients with NSCLC, tumors harbor activating genomic alterations in the corresponding kinase region of genes including EGFR and BRAF that result in constitutive activation and have been identified as driver mutations (see, e.g., Gridelli et al, Nat Rev Dis Prim. 2015, which is incorporated by reference herein). Activating mutations for EGFR include, but are not limited to: G719X; Exon19 deletions; V765A; T783A; V774A; S784P; L858R & L861X. Activating mutations for BRAF include, but are not limited to: V600E; L601G; K601E; L597V/Q/R and G469V/S/R/E/A). Additionally, chromosomal rearrangements between both ALK and ROS1 and fusion partners, have been identified as drivers. This results from either ALK or ROS1's kinase domain being put under the control of a new promoter. Variants include EML4-ALK, TFG-ALK, KIF5B-ALK, CD74-ROS1, SLC34A2-ROS1, SDC4-ROS1 and EZR-ROS1. Targeted therapies directed against these activating alterations in EGFR, ALK, ROS1 and BRAF have been approved for use in patients harboring these activating mutations and fusions, and thus, these are described as "actionable" mutations. NSCLC patients harboring EGFR and BRAF activating mutations or ALK rearrangements are believed to be associated with low overall response rates to PD-1/PD-L1 inhibitors. As such, in some embodiments, the patient may be assessed for actionable mutations EGFR, ALK, ROS1 and BRAF. If such a mutation is detected then a PD-1/PD-L1 immune checkpoint inhibitor is not administered. Rather a therapy that is appropriate for the mutation may be administered. For example, erlotinib (Tarceva), afatinib (Gilotrif), gefitinib (Iressa) or osimertinib (Tagrisso) may be administered to patients having an activating mutation in EGFR, crizotinib (Xalkori), ceritinib (Zykadia), alectinib (Alecensa) or brigatinib (Alunbrig) may be administered to patients having an an ALK fusion, crizotinib (Xalkori), entrectinib (RXDX-101), lorlatinib (PF-06463922), crizotinib (Xalkori), entrectinib (RXDX-101), lorlatinib (PF-06463922), ropotrectinib (TPX-0005), DS-6051b, ceritinib, ensartinib or cabozantinib may be administered to patients having an an ROS1 fusion, and dabrafenib (Tafinlar) or trametinib (Mekinist) may be administered to patients having an activating mutation in BRAF. In any embodiment, the activating mutations in EGFR and BRAF may comprise: G719X, exon19 deletions, V765A, T783A, V774A, S784P, L858R and L861X in EGFR and V600E; L601G; K601E; L597V/Q/R and G469V/S/R/E/A in BRAF. Likewise, in any embodiment the rearrangements in ALK and ROS1 may comprise EML4-ALK, TFG-ALK, KIF5B-ALK, CD74-ROS1, SLC34A2-ROS1, SDC4-ROS1 and EZR-ROS1 fusions.

A patient that, based on the analysis of the patient's cell-free DNA, appears to be EGFR activating mutation-negative, BRAF activating mutation-negative, ALK rearrangement-negative and ROS1 rearrangement-negative and has one or more nucleotide transversions in the coding sequences of TP53 and KRAS and no predicted loss of function mutations in PTEN or STK11 may be treated with an immune checkpoint inhibitor.

In alternative embodiments, any of the methods described or claimed above or below can be practiced on DNA isolated from a tissue biopsy, e.g., a section of tissue, an aspirate, or a sample of cells collection of a tumor. In some embodiments, the biopsy may comprise cells or a tissue sample of lung, e.g., a site or circulating or migrating cells of NSCLC. The sample may include any extract or partial or whole fractionation of cell or tissue sample of lung, e.g., on site or circulating or migrating cells of NSCLC.

In some embodiments, the method may further comprise sequencing a set of non-coding sequences, and, in some cases, counting the total number of nucleotide transversions in those sequences.

Figure 1:
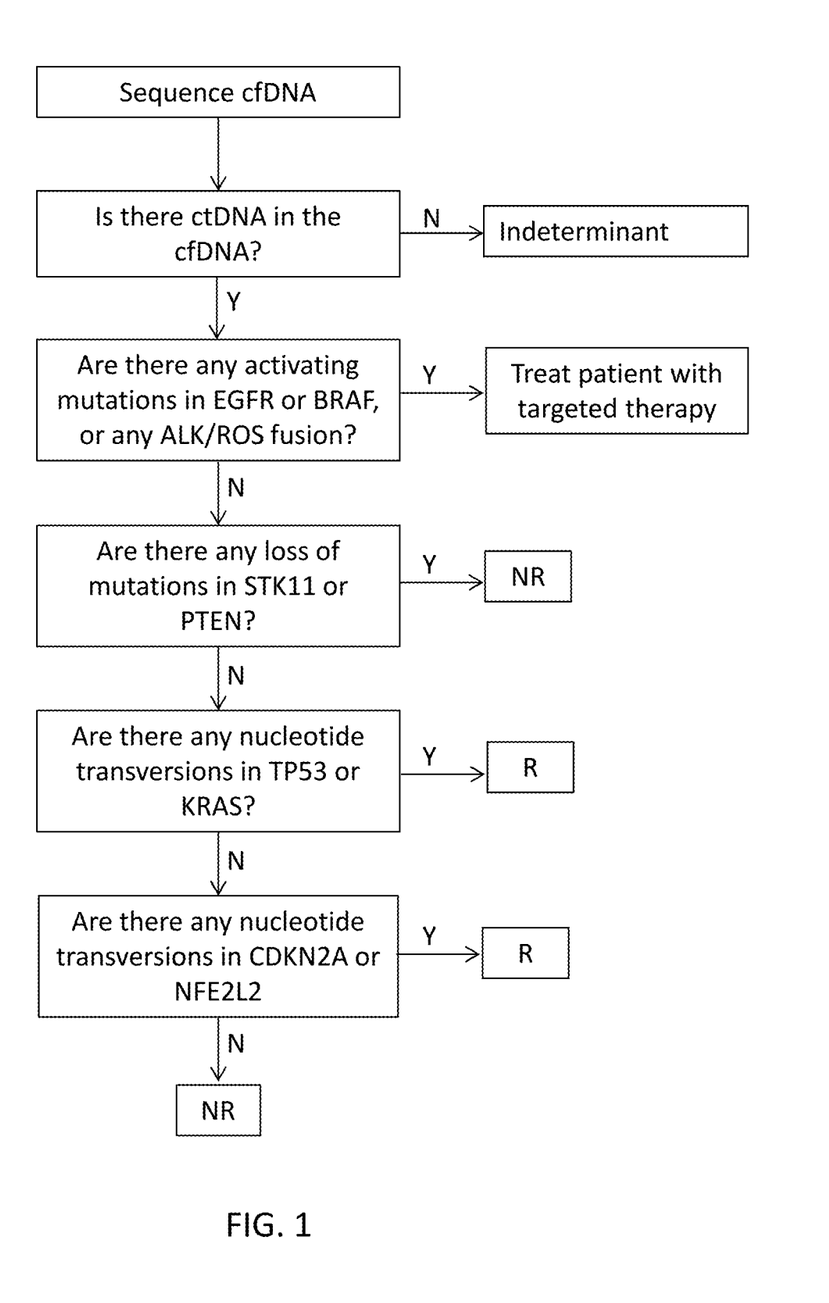

A flow chart illustrating an exemplary implementation of the method is shown in FIG. 1. In this implementation, after sequencing cfDNA, the sequences are analyzed to determine if there is any circulating tumor DNA in the cfDNA. ctDNA can be identified because it contains relatively low frequency mutations (e.g., less than 10% and occasionally higher). If there is no ctDNA is detected in the cfDNA, then the patient may be indicated as an "indeterminant", which indicates that it is unpredictable whether the patient will respond or will not respond to any targeted therapy or immune checkpoint inhibition. In the implementation shown, the sequences may be screened for actionable mutations (i.e., mutations in genes such as, e.g., EGFR, BRAF, ALK and ROS1, as described above, for which a target treatment is already available). Cancers associated with these mutations are generally not responsive to immune checkpoint inhibition unless there is a nucleotide transversion in KRAS or TP53. If there are no actionable mutations EGFR, BRAF, ALK and ROS1, then the sequences for PTEN and STK11 can be screened for loss of function mutations. If there are no predicted loss of function mutations in PTEN and STK11, then the presence of nucleotide transversions (or a score representing the same) in the coding sequences of TP53 and KRAS (and, optionally, CDKN2A and NFE2L2) are determined. If nucleotide transversions are identified or if the total number of nucleotide transversions is above a threshold, then the patient should be indicated as being responsive to immune checkpoint inhibition. Other nucleotide changes may contribute to the decision about whether a patient may be indicated as being responsive to immune checkpoint inhibition, in addition to those described above. In some embodiments, results obtained from this workflow may be expressed as a "score".

A brief description of some of the genes that can be analyzed in this method is set forth below.

TP53 is the gene that encodes the tumor suppressor p53. In humans, the TP53 gene is located on the short arm of chromosome 17 (17p13.1). The gene spans 20 kb, with a non-coding exon 1 and a very long first intron of 10 kb. The coding sequence contains five regions showing a high degree of conservation in vertebrates, predominantly in exons 2, 5, 6, 7 and 8. TP53 orthologs have been identified in most mammals for which complete genome data are available. In humans, a common polymorphism involves the substitution of an arginine for a proline at codon position 72. Many studies have investigated a genetic link between this variation and cancer susceptibility. See, e.g., Matlashewski et al, The EMBO Journal. 1984 3: 3257-62. The sequence of the human TP53 gene and its structure are set forth in entry 7157 in NCBI's gene database; NCBI Reference Sequence: NG_017013.2.

KRAS is a Kirsten ras oncogene homolog from the mammalian ras gene family and encodes a protein that is a member of the small GTPase superfamily. Several mutations are known can activate this protein (see, e.g., Karachaliou et al Clin Lung Cancer. 2013 14: 205-14). Alternative splicing leads to variants encoding two isoforms that differ in the C-terminal region. KRAS is also known as K-Ras 2, Ki-Ras, c-K-ras, and c-Ki-ras. Human cells harbor the KRAS gene at chromosomal band 12p12.1. See, e.g., Tsuchida et al, Oncotarget. 2016 7: 46717-33. The sequence of the human KRAS gene and its structure are set forth in entry 3845 in NCBI's gene database; NCBI Reference Sequence: NG_007524.1.

BRAF is the human gene that encodes a protein called B-Raf. The gene is also referred to as proto-oncogene B-Raf and v-Raf murine sarcoma viral oncogene homolog B, while the protein is more formally known as serine/threonine-protein kinase B-Raf. The BRAF gene is located on chromosome 7q34, and covers approximately 190 kb. It contains at least 19 exons and encodes a full-length transcript of 2,510 bp (NM_00433). At least seven variant transcripts have been identified, which are products of alternative splicing. From these various transcripts, several proteins are translated, including the full-length, 94-95 kD, 783 amino acid product. See, e.g., Sithanandam et al, Oncogene 1990 5: 1775-80; and Meyer et al Journal of Carcinogenesis 2003 2, 7. The sequence of human BRAF and its structure are set forth in entry 673 in NCBI's gene database; NCBI Reference Sequence: NG_007873.3.

EGFR encodes a transmembrane glycoprotein that is a member of the protein kinase superfamily. The gene maps to 7p11.2. The EGFR gene contains 28 exons and spans nearly 200 kb. Intron 1 spans 123 kb. The gene contains several repeat elements, including SINEs and LINEs, as well as a trinucleotide (TGG/A) repeat-rich region in intron 15, and 2 long CA repeats in intron 27. The sequence of the human EGFR gene and its structure are set forth in entry 1956 in NCBI's gene database; NCBI Reference Sequence: NG_007726.3. See, e.g., Zhang et al J Med Genet. 2007 44: 166-72.

ALK encodes a receptor tyrosine kinase, which belongs to the insulin receptor superfamily. ALK is situated on the short arm of chromosome 2 (2p23.2). The gene contains over 30 distinct introns and transcription produces about 8 different mRNAs, with several alternatively spliced variants and unspliced forms. The sequence of the human ALK gene and its structure are set forth in entry 427 in NCBI's gene database; NCBI Reference Sequence: NC_000002.12. See, e.g., Figueiredo-Pontes et al J Thorac Oncol. 2014 February; 9(2): 248-253.

The CDKN2A gene resides on chromosome 9 at the band 9p21 and contains 8 exons. This gene encodes two proteins, p16 and p14ARF, which are transcribed from the same second and third exons but alternative first exons: p16 from exon 1α and ARF from exon 1β. As a result, they are translated from different reading frames and therefore possess completely different amino acid sequences. In addition to p16 and ARF, this gene produces 4 other isoforms through alternative splicing. See, e.g., Stone et al, Cancer Res. 1995 55: 2988-2994. The sequence of the human CDKN2A gene and its structure are set forth in entry 1029 in NCBI's gene database; NCBI Reference Sequence: NG_007485.1.

The NFE2L2 gene encodes nuclear factor (erythroid-derived 2)-like 2, also known as NFE2L2 or Nrf2. The NFE2L2 gene is located on 2q31. NFE2L2 gene contains 5 exons and spans over 11 kb. The first intron is over 6 kb long. See, e.g., Moi et al Proc. Nat. Acad. Sci. 1994 91: 9926-9930. The sequence of the human NFE2L2 gene and its structure are set forth in entry 4780 in NCBI's gene database; NCBI Reference Sequence: NM_001145412.3.

The PTEN gene encodes phosphatase and tensin homolog (PTEN). The gene is thought to contain about 12 distinct introns, and transcription of the gene produces 12 different mRNAs, 7 alternatively spliced variants and 5 unspliced forms. The gene is located at chromosome 10q23. See, e.g., Li et al Science 1997 275: 1943-7. The sequence of the human PTEN gene and its structure are set forth in entry 5728 in NCBI's gene database; NCBI Reference Sequence: NG_007466.2.

The STK11 gene, also known as LKB1 or PJS, encodes Serine/threonine kinase 11 (STK11) also known as liver kinase B1 (LKB1) or renal carcinoma antigen NY-REN-19. The gene is located within a region on chromosome 19p13.3 and is thought to contain 18 distinct introns. See, e.g., Masuda et al Hum Genome Var. 2016 3: 16002. The sequence of the human STK11 gene and its structure are set forth in entry 6794 in NCBI's gene database; NCBI Reference Sequence: NG_007460.2.

The sequencing step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads. As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps. Nanopore sequencing could be employed in certain cases.

In some embodiments, the patient may have a cancer that is immunologically mediated, such as lung cancer including non-small cell lung cancer (NSCLC) or small cell lung cancer, melanoma, renal cell carcinoma or a lymphoma. In some cases, the patient may not have colon, breast, prostate, pancreas, or liver cancer (which are not generally susceptible to immunotherapy).

In some embodiments, the method may comprise providing a report indicating whether there are: i. nucleotide transversions in the coding sequences of TP53 and KRAS, relative to reference sequences of TP53 and KRAS, and, optionally, ii. predicted loss of function mutations in PTEN and STK11, iii. activating mutations in EGFR and BRAF, and/or iv. rearrangements in ALK and ROS1. In addition or in the alternative, the report may indicate a score based on the foregoing analysis that indicates the likelihood that a patient will be responsive to therapy by an immune checkpoint inhibitor. The score may be numerical or alphabetical, or may use descriptors such as "high", "medium" or "low", or symbols such as "+++", "++", "+" or "−", for example). In some embodiments, a report may provide options for approved (e.g., FDA approved) therapies, e.g., immune checkpoint inhibitors, for cancers that are associated with the mutation(s) identified in the sample. This information can guide treatment decisions made by a physician, In some embodiments, the report may be in an electronic form, and the method comprises forwarding the report to a remote location, e.g., to a doctor or other medical professional to help identify a suitable course of action, e.g., to identify a suitable therapy for the subject. The report may be used along with other metrics to determine whether the subject may be susceptible to immune checkpoint inhibition.

In any embodiment, a report can be forwarded to a "remote location", where "remote location," means a location other than the location at which the sequences are analyzed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet, including email transmissions and information recorded on websites and the like. In certain embodiments, the report may be analyzed by an MD or other qualified medical professional, and a report based on the results of the analysis of the sequences may be forwarded to the patient from which the sample was obtained.

In some embodiments, the method may comprise providing at least one option for a treatment by an immune checkpoint inhibitor based on: (i) whether there are nucleotide transversions in the coding sequences of TP53 and KRAS, and, optionally, CDKN2A and NFE2L2, (ii) whether there are any loss of function mutations in PTEN and STK11, (iii) whether there are any activating mutations in EGFR and BRAF, and (iv) whether there are any rearrangements in ALK and ROS1.

In some embodiments, a patient may be selected for treatment by an immune checkpoint inhibitor if the total number of nucleotide transversions is above a threshold and there are no predicted loss of function mutations in PTEN and STK11, no activating mutations in EGFR and BRAF, and no rearrangements in ALK and ROS1. For example, if the total number of nucleotide transversions is high relative to other patients and there are no loss of function mutations in PTEN and STK11, no activating mutations in EGFR and BRAF, and no rearrangements in ALK and ROS1, then the patient may be selected for immune checkpoint therapy. In these embodiments, even a single nucleotide transversion can indicate that the patient is susceptible to immune checkpoint therapy. As such, in some embodiments, the threshold can be 1. In other embodiments, the patient will only be recommended for immune checkpoint therapy if there are at least 1, at least 2, at least 3, at least 4, at least 5, or at least 10 nucleotide transversions.

The method described above and below may comprise determining whether there are or counting the total number of A to T transversions, determining whether there are or counting the total number of T to A transversions, determining whether there are or counting the total number of A to C transversions, determining whether there are or counting the total number of C to A transversions, determining whether there are or counting the total number of G to T transversions, determining whether there are or counting the total number of T to G transversions, and determining whether there are or counting the total number of G to C transversions, or any combination thereof (e.g., determining whether there are or counting the total number of A to T, T to A, A to C and C to A transversions).

Also provided is a method for treating cancer. In this method, the method may comprise: (a) determining, in a sample of cfDNA from a cancer patient: (i) whether there are nucleotide transversions in the coding sequences of TP53 and KRAS, and, optionally, CDKN2A and NFE2L2, (ii) whether there are any loss of function mutations in PTEN and STK11, (iii) whether there are any activating mutations in EGFR and BRAF, and (iv) whether there are any rearrangements in ALK and ROS1, or receiving a report indicating the same, where this analysis may be done using the method described above; and (b) identifying the patient as a candidate for treatment with an immune checkpoint inhibitor if there are one or more nucleotide transversions in the coding sequences of TP53 or KRAS, no predicted loss of function mutations in PTEN and STK11, no activating mutations in EGFR and BRAF, and no rearrangements in ALK and ROS1. In some embodiments, the method may comprise administering the immune checkpoint inhibitor to the patient.

In this method, the immune checkpoint inhibitor may be an antibody, e.g., an anti-CTLA-4 antibody, anti-PD1 antibody, an anti-PD-L1 antibody, an anti-TIM-3 antibody, an anti-VISTA antibody, an anti-LAG-3 antibody, an anti-IDO antibody, or an anti-KIR antibody, although others are known. In some embodiments, the immunotherapy may also include a co-stimulatory antibody such as an antibody against CD40, GITR, OX40, CD137, or ICOS, for example. In some embodiments, the antibody may be an anti-PD-1 antibody, an anti-PD-L1 antibody or an anti-CTLA-4 antibody. Examples of such antibodies include, but are not limited to: Ipilimumab (CTLA-4), Nivolumab (PD-1), Pembrolizumab (PD-1), Atezolizumab (PD-L1), Avelumab (PD-L1), and Durvalumab (PD-L1). These therapies may be combined with one another with other therapies. In some embodiments, the dose administered may be in the range of 1 mg/kg to 10 mg/kg, or in the range of 50 mg to 1.5 g every few weeks (e.g., every 3 weeks), depending on the weight of the patient.

In certain embodiments, the patient will be treated with the immune checkpoint inhibitor without knowing the PD1, CTLA-4, TIM-3, VISTA, LAG-3, IDO or KIR status of the tumor.

Also provided is a method for monitoring treatment of a cancer that has been treated with an immune checkpoint inhibitor. In some embodiments, the method may comprise (a) determining the allele frequency (AF) of nucleotide transversions in the coding sequences of at least TP53 and KRAS (e.g., at least TP53, KRAS, CDKN2A and NFE2L2)

in a sample of cfDNA from a cancer patient at a first time point, or receiving a report indicating the same; (b) determining the allele frequency (AF) of nucleotide transversions in the same coding sequences in a sample of cfDNA from the cancer patient at a second time point, or receiving a report indicating the same; and (c) comparing the AF of nucleotide transversions at the first time point to the AF of nucleotide transversions at the second time point, thereby monitoring the treatment of the cancer. A decrease in the AF of nucleotide transversions of at least 30% (e.g., at least 40% or at least 50%) indicates that the patient is responsive to the immune checkpoint inhibitor and a decrease of less than 30% or an increase in the AF nucleotide transversions or increases in the AF of nucleotide transitions indicates that the patient is not responding to the immune checkpoint inhibitor.

A method for predicting a phenotype, comprising: (a) analyzing the nucleotide transversions and/or transitions from a plurality of cfDNA samples using the method, wherein the cfDNA samples are isolated from different patients having a known phenotype; and (b) identifying nucleotide transversions that correlate with the phenotype. The phenotype may be a disease, condition or clinical outcome. The nucleotide transversions and/or transitions may be diagnostic, prognostic or theranostic. In some embodiments, this method may comprise comparing the distribution of nucleotide transversions or transitions from a first patient population that is responsive to an immune checkpoint inhibitor to the distribution of nucleotide transversions or transitions from a patient population that is non-responsive to an immune checkpoint inhibitor and, optionally, estimating the goodness of fit for each of the distributions in order to predict predict the response status. In some embodiments, the method may comprise (i) comparing the computed distribution of transversion/transition in each patient in two reference populations of responders/non-responder (ii) and estimating the goodness of-fit of the data to each of these two populations is estimated in order to quantitatively predict the response status.

As would be readily appreciated, many steps of the method, e.g., the sequence processing steps and the generation of a report indicating the total number of transversions, may be implemented on a computer. As such, in some embodiments, the method may comprise executing an algorithm that calculates the likelihood of whether a patient will be responsive to immune checkpoint inhibitor based on: (i) whether there are nucleotide transversions in the coding sequences for at least TP53 and KRAS (e.g., TP53, KRAS, CDKN2A and NFE2L2) or the total number of the same and, optionally, (ii) whether there are any loss of function mutations in PTEN and STK11, (iii) whether there are any activating mutations in EGFR and BRAF, and (iv) whether there are any rearrangements in ALK and ROS1, and outputting the likelihood. In some embodiments, this method may comprise inputting the sequences into a computer and executing an algorithm that can calculate the likelihood using the input measurements.

In computer-related embodiments, a system may include a computer containing a processor, a storage component (i.e., memory), a display component, and other components typically present in general purpose computers. The storage component stores information accessible by the processor, including instructions that may be executed by the processor and data that may be retrieved, manipulated or stored by the processor.

The storage component includes instructions for providing a score using the measurements described above as inputs. The computer processor is coupled to the storage component and configured to execute the instructions stored in the storage component in order to receive patient data and analyze patient data according to one or more algorithms. The display component may display information regarding the diagnosis of the patient.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the diagnostic system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

EMBODIMENTS

Embodiment 1

A method for treating a patient with an immune checkpoint inhibitor, wherein the patient is suffering from cancer, the method comprising:

(a) obtaining or having obtained a sample of blood from the patient;

(b) performing or having performed a sequencing assay on cell-free DNA (cfDNA) from the sample to determine if the cell-free DNA comprises one or more nucleotide transversions in the coding sequences of TP53 and KRAS, relative to reference sequences of TP53 and KRAS; and (c) if the patient has one or more nucleotide transversions in the coding sequences of TP53 and KRAS, then administering an effective amount of the immune checkpoint inhibitor to the patient.

Embodiment 2

The method of embodiment 1, wherein the sequencing assay further determines if the cell-free DNA comprises one or more nucleotide transversions in the coding sequences of CDKN2A and NFE2L2.

Embodiment 3

The method of any prior embodiment, wherein the method comprises:

(a) obtaining or having obtained a sample of blood from the patient;
(b) performing or having performed a sequencing assay on cell-free DNA (cfDNA) from the sample to determine if the cell-free DNA comprises:
  i. nucleotide transversions in the coding sequences of TP53 and KRAS, relative to reference sequences of TP53 and KRAS, and
  ii. predicted loss of function mutations in PTEN and STK11, and
(c) if the patient has one or more nucleotide transversions in the coding sequences of TP53 and KRAS, and no predicted loss of function mutations in PTEN and STK11, then administering an effective amount of the immune checkpoint inhibitor to the patient.

Embodiment 4

The method of any prior embodiment, wherein the method comprises:
(a) obtaining or having obtained a sample of blood from the patient;
(b) performing or having performed a sequencing assay on cell-free DNA (cfDNA) from the sample to determine if the cell-free DNA comprises:
  i. nucleotide transversions in the coding sequences of TP53 and KRAS, relative to reference sequences of TP53 and KRAS,
  ii. predicted loss of function mutations in PTEN and STK11,
  iii. activating mutations in EGFR and BRAF, and
  iv rearrangements in ALK and ROS1; and
(c) if the patient has one or more nucleotide transversions in the coding sequences of TP53 and KRAS, no predicted loss of function mutations in PTEN and STK11, no activating mutations in EGFR and BRAF and no rearrangements in ALK and ROS1, then administering an effective amount of the immune checkpoint inhibitor to the patient.

Embodiment 5

The method of any prior embodiment, wherein the patient has non-small cell lung cancer (NSCLC).

Embodiment 6

The method of any prior embodiment, wherein the method comprises:
receiving a report indicating that there is at least one transversion in TP53 or KRAS and, optionally, whether there are any loss of function mutations in PTEN or STK11, whether there are activating mutations in EGFR or BRAF and/or whether there are rearrangements in ALK or ROS1, or a score indicating the same.

Embodiment 7

The method of any prior embodiment, wherein the the sequencing assay is done by:
(i) amplifying the coding sequences of the genes in a multiplex PCR reaction in which at least 10 amplicons are amplified; and
(ii) sequencing the amplicons.

Embodiment 8

The method of any prior embodiment, wherein the sequencing assay comprises determining if there are A to T transversions, determining if there are T to A transversions, determining if there are A to C transversions, determining if there are C to A transversions, determining if there are G to T transversions, determining if there are T to G transversions, determining if there are G to C transversions, and determining if there are C to G transversions
or any combination thereof.

Embodiment 9

The method of any prior embodiment, wherein the immune checkpoint inhibitor is an antibody.

Embodiment 10

The method of embodiment 9, wherein the antibody is an anti-CTLA-4 antibody, anti-PD1 antibody, an anti-PD-L1 antibody, an anti-TIM-3 antibody, an anti-VISTA antibody, an anti-LAG-3 antibody, an anti-IDO antibody, or an anti-KIR antibody.

Embodiment 11

The method of any of embodiments 9 or 10, wherein the antibody is an anti-PD-1 antibody or an anti-PD-L1 antibody.

Embodiment 12

A method for analyzing cell free DNA (cfDNA) from the bloodstream of a cancer patient, comprising:
(a) sequencing at least part of the coding sequences of TP53 and KRAS in a sample of the cfDNA;
(b) analyzing the sequences obtained in step (a) to identify nucleotide transversions in the coding sequences of the genes, relative to reference sequences of the genes.

Embodiment 13

The method of embodiment 12, further comprising:
(c) counting the total number of nucleotide transversions identified in step (b).

Embodiment 14

The method of embodiments 12 or 13, wherein step (a) comprises:
sequencing at least part of the coding sequences of TP53, KRAS, and, optionally, CDKN2A and NFE2L2 in the sample of cfDNA.

Embodiment 15

The method of any of embodiments 12-14, wherein the method comprises:
(d) sequencing at least part of the coding sequences of PTEN and STK11 in the sample of cfDNA and analyzing the sequences to determine if there are any loss of function mutations in PTEN or STK11;
(e) sequencing at least part of the coding sequences of EGFR and BRAF in the sample of cfDNA and analyzing the sequences to determine if there are any activating mutations in EGFR or BRAF; and
(f) sequencing at least part of ALK and ROS1 in the sample of cfDNA and analyzing the sequences to determine if there are any rearrangements in ALK or ROS1.

Embodiment 16

The method of any of embodiments 12-15, wherein the patient has non-small cell lung cancer (NSCLC).

Embodiment 17

The method of any of embodiments 12-16, further comprising:
providing a report indicating the number of transversions in the genes of step (a) and, optionally, whether there are any loss of function mutations in PTEN or STK11, whether there are activating mutations in EGFR or BRAF and/or whether there are rearrangements in ALK or ROS1, or a score indicating the same.

Embodiment 18

The method of any of embodiments 12-16, further comprising:
providing a report indicating that there are transversions in the genes of step (a) and, optionally, whether there are any loss of function mutations in PTEN or STK11, whether there are activating mutations in EGFR or BRAF and/or whether there are rearrangements in ALK or ROS1, or a score indicating the same.

Embodiment 19

The method of embodiment 17 or 18, further comprising forwarding the report to remote location.

Embodiment 20

The method of any of embodiments 12-19, further comprising providing a recommendation for a treatment by an immune checkpoint inhibitor based on:
(i) whether there are nucleotide transversions in the coding sequences of the genes of (a) and
(ii) whether there are any loss of function mutations in PTEN and STK11,
(iii) whether there are any activating mutations in EGFR and BRAF, and
(iv) whether there are any rearrangements in ALK and ROS1;
wherein treatment by an immune checkpoint inhibitor is recommended if there are transversions in the coding sequences of the genes of (a), there are no predicted loss of function mutations in PTEN and STK11, there are no activating mutations mutations in EGFR and BRAF; and there are no rearrangements in ALK and ROS1.

Embodiment 21

The method of any of embodiments 12-19, further comprising providing an option for treatment with an approved treatment by an immune checkpoint inhibitor based on:
(i) whether there are nucleotide transversions in the coding sequences of the genes of (a) and
(ii) whether there are any loss of function mutations in PTEN and STK11,
(iii) whether there are any activating mutations in EGFR and BRAF, and
(iv) whether there are any rearrangements in ALK and ROS1,
wherein treatment by an immune checkpoint inhibitor is listed as an option if there are transversions in the coding sequences of the genes of (a), there are no predicted loss of function mutations in PTEN and STK11, there are no activating mutations mutations in EGFR and BRAF; and there are no rearrangements in ALK and ROS1.

Embodiment 22

The method of any of embodiments 12-21, wherein the sequencing is done by:
(i) amplifying the coding sequences of the genes in a multiplex PCR reaction in which at least 10 amplicons are amplified; and
(ii) sequencing the amplicons.

Embodiment 23

The method of any of embodiments 12-22, wherein the counting step (c) comprises counting the total number of A to T transversions, counting the total number of T to A transversions, counting the total number of A to C transversions, counting the total number of C to A transversions, counting the total number of G to T transversions, counting the total number of T to G transversions, counting the total number of G to C transversions, and counting the total number of C to G transversions, or any combination thereof.

Embodiment 24

The method of any of embodiments 12-23, wherein the counting step (c) comprises determining if there are A to T transversions, determining if there are T to A transversions, determining if there are A to C transversions, determining if there are C to A transversions, determining if there are G to T transversions, determining if there are T to G transversions, determining if there are G to C transversions, and determining if there are C to G transversions, or any combination thereof.

Embodiment 25

A method for treating cancer, comprising:
(a) determining, in a sample of cfDNA from a cancer patient:
   (i) whether there are any nucleotide transversions in the coding sequences of at least part of the coding sequences of TP53 and KRAS; and
   (ii) whether there are any loss of function mutations in PTEN and STK11, or receiving a report indicating the same; and
(b) identifying the patient as a candidate for treatment with an immune checkpoint inhibitor if there are nucleotide transversions and there are no predicted loss of function mutations in PTEN and STK11.

Embodiment 26

The method of embodiment 25, wherein the patient is identified as a candidate for treatment with an immune checkpoint inhibitor if there are transversions in the coding sequences of the genes of (a), there are no predicted loss of function mutations in PTEN and STK11, there are no activating mutations mutations in EGFR and BRAF; and there are no rearrangements in ALK and ROS1.

Embodiment 27

The method of embodiment 26, further comprising administering the immune checkpoint inhibitor to the patient.

Embodiment 28

The method of embodiments 27, wherein the immune checkpoint inhibitor is an antibody.

Embodiment 29

The method of any of embodiments 26-28, wherein the antibody is an anti-CTLA-4 antibody, anti-PD1 antibody, an anti-PD-L antibody, an anti-TIM-3 antibody, an anti-VISTA antibody, an anti-LAG-3 antibody, an anti-IDO antibody, or an anti-KIR antibody.

Embodiment 30

The method of any of embodiments 26-29, wherein the antibody is a PD-1 antibody or PD-L1 antibody.

Embodiment 31

The method of any of embodiments 26-30, wherein the cancer patient has non-small cell lung cancer.

Embodiment 32

The method of any of embodiments 26-31, wherein the report indicates the total number of nucleotide transversions in the at least part of the coding sequences of at least TP53 and KRAS, CDKN2A and NFE2L2, or a score indicating the same.

Embodiment 33

The method of any of embodiments 26-32, wherein the total number of nucleotide transversions of (a)(i) is the sum of the total number of A to T transversions, the total number of T to A transversions, the total number of A to C transversions, the total number of C to A transversions, the total number of G to T transversions, the total number of T to G transversions, the total number of G to C transversions, and the total number of C to G transversions.

Embodiment 34

The method of any of embodiments 26-33, wherein the sequencing also comprises a set of non-coding sequences.

Embodiment 35

A method for monitoring treatment of a cancer that has been treated with an immune checkpoint inhibitor, comprising:
(a) determining the allele frequency of one or more nucleotide transversions in the coding sequences of at least TP53 and KRAS in a sample of cfDNA from a cancer patient at a first time point, or receiving a report indicating the same;
(b) determining the allele frequency of the one or more nucleotide transversions in the coding sequences of at least TP53 and KRAS in a sample of cfDNA from the cancer patient at a second time point, or receiving a report indicating the same; and
(c) comparing the allele frequency of the one or more nucleotide transversions at the first time point to the allele frequency of the one or more nucleotide transversions at the second time point, thereby monitoring the treatment of the cancer.

Embodiment 36

The method of embodiment 36, wherein, a decrease in the allele frequency of nucleotide transversions of at least 30% indicates that the patient is responding to the immune checkpoint inhibitor and a decrease of less than 30% or an increase in the allele frequency of nucleotide transversions indicates that the patient is not responding to the immune checkpoint inhibitor.

Embodiment 37

The method of any of embodiments 35-36, wherein the steps (a) and (b) comprise determining the allele frequency of nucleotide transversions in the coding sequences of at least TP53, KRAS, CDKN2A and NFE2L2.

Embodiment 38

A method for predicting a phenotype, comprising:
(a) analyzing the nucleotide transversions and/or transitions from a plurality of cfDNA samples using the method of any of embodiments 12-24, wherein the cfDNA samples are isolated from different patients having a known phenotype; and
(b) identifying nucleotide transversions, or a number of the same, that correlate with the phenotype.

Embodiment 39

The method of embodiment 38, wherein the phenotype is a disease, condition or clinical outcome.

Embodiment 40

The method of embodiment 39, wherein the nucleotide transversions and/or transitions are diagnostic, prognostic or theranostic.

Embodiment 41

The method of any of embodiments 38-40, wherein the method comprises:
comparing the distribution of nucleotide transversions or transitions from a first patient population that is responsive to an immune checkpoint inhibitor to the distribution of nucleotide transversions or transitions from a patient population that is non-responsive to an immune checkpoint inhibitor.

Embodiment 42

The method of embodiment 41, further comprising estimating the goodness of fit for each of the distributions in order to predict predict the response status.

EXAMPLES

Aspects of the present teachings can be further understood in light of the following examples, which should not be construed as limiting the scope of the present teachings in any way.

Example 1

Figure 2:
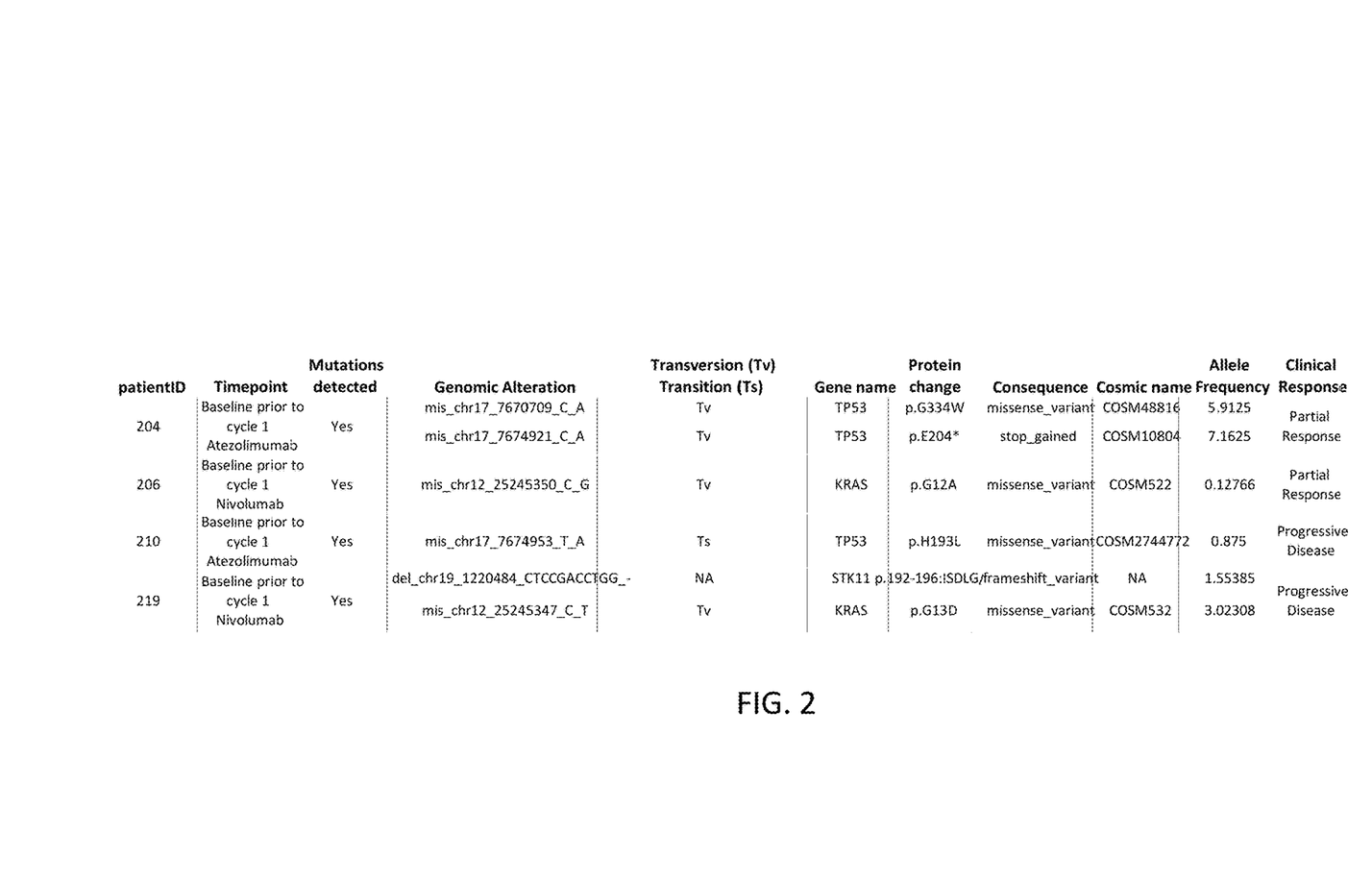
FIG. 2 provides examples of the ability of the sequencing workflow used to identify and differentiate specific genomic alterations (transversions vs transitions) in the target genes. Furthermore, response to clinical intervention with PD-1/PD-L1 targeting therapies correlated with the presence of these specific alterations with benefit being derived when those alterations where transversion in nature and lack of clinical benefit demonstrated when the alterations were due to transitions or alterations in STK11 were present.

Identification of Specific Genomic Alterations and Association with Clinical Benefit to PD-1/PD-L1 Targeting Therapies Cell-free DNA (cfDNA) was extracted from plasma isolated from patients' blood collected prior to initial treatment with PD-1/PD-L1 targeting therapies such as nivolumab or atezolimumab for advanced stage NSCLC. Genomic alterations present in the circulating tumor DNA (ctDNA) fraction of cfDNA were identified using the InVision™ Amplicon-based plasma NGS platform which sequences the target genes of interests using gene specific primers designed to hotspots and entire coding regions. Sequencing files were analysed using Inivata's proprietary Somatic Mutation Analysis (ISoMA) pipeline. Mutations were detected and reported such as those in FIG. 2. Mutations were classified as a transition mutation if they were a C>T, T>C, A>G or G>A change. They were classified as a transversion if they were an A>C, C>A, G>T, T>G, A>T, T>A, G>C or C>G change.

Example 2

Efficacy of Nivolumab in Patients with High Vs Low Score

In the following examples, the terms "High" and "Low" are used to indicate a patient's responsiveness to immune checkpoint inhibition by an anti-PD-1 or an anti-PD-L1 antibody. A patient assigned a "High" score has a higher likelihood of responding to immune checkpoint inhibition by an anti-PD-1 or an anti-PD-L1 antibody whereas a patient assigned a "Low" score has a lower likelihood of responding to immune checkpoint inhibition by an anti-PD-1 or an anti-PD-L1 antibody.

Figure 3:
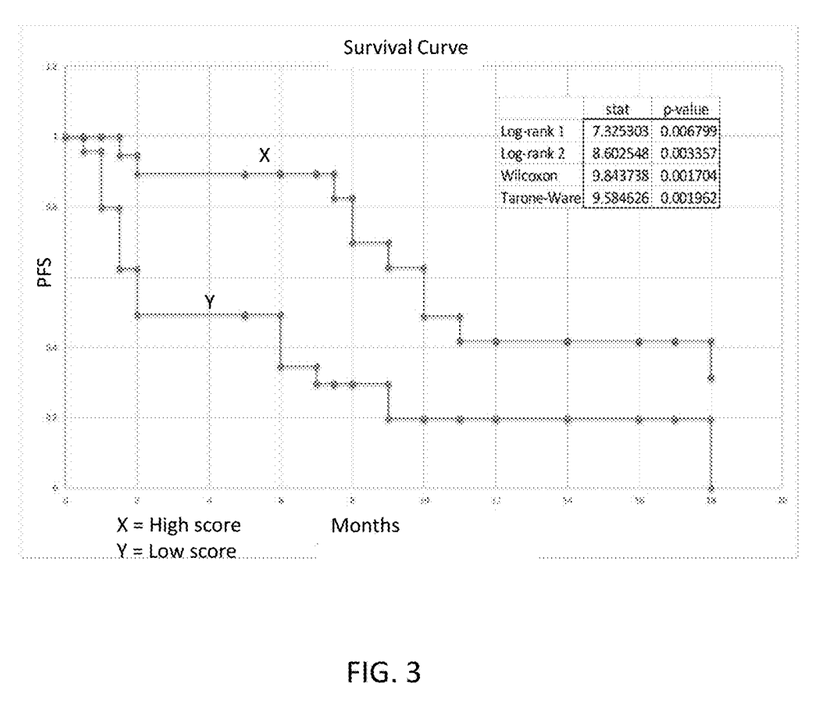
FIG. 3 shows a Kaplan-Meier plot of patients with a High score (X) or Low score (Y).

Plasma from 45 patients diagnosed with advanced stage NSCLC undergoing treatment for progressive disease with nivolumab was analyzed using the InVision™ NGS platform to characterize alterations in ctDNA. Samples were assigned either an High (n=20) or Low (n=25) score based on the algorithm described in FIG. 1 as outlined above and below. Patients with no detectable ctDNA were classified as indeterminant. Patients with actionable EGFR or BRAF mutations, or either ALK or ROS1 fusions were recommended targeted therapy and classified as Low. Patients with predicted loss of function mutations in genes PTEN or STK11 detected were classified as Low. Of the remaining patients, those identified with the presence of transversions in the target list of genes (TP53, KRAS, CDKN2A, NFE2L2) were classified as High. The remaining patients with just transition mutations were classified as Low. Patients with a High score (transversions) showed significantly longer progression-free survival than patients with an Low score (lack of transversions) when treated with nivolumab (FIG. 3).

Example 3

Monitoring Response to Therapy

Figure 4:
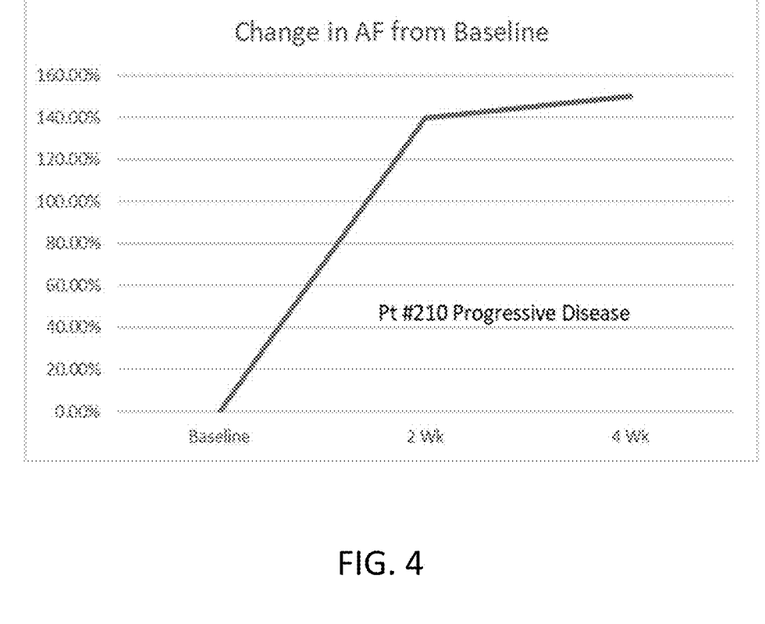
FIG. 4 shows mutant allele frequencies monitored throughout treatment in a patient who demonstrated progressive disease while on therapy with atezolimumab.

In this example, serial plasma samples were collected beginning at base line prior to initial therapy and then subsequent collections over a period of 2 months. Changes from base line in the allele frequency (AF) of genomic alterations in ctDNA were calculated and plotted as shown. In the first figure from a patient who demonstrated progressive disease while on therapy with atezolimumab, ctDNA AFs increased >2-fold from baseline to week 2 (FIG. 4).

Figure 5:
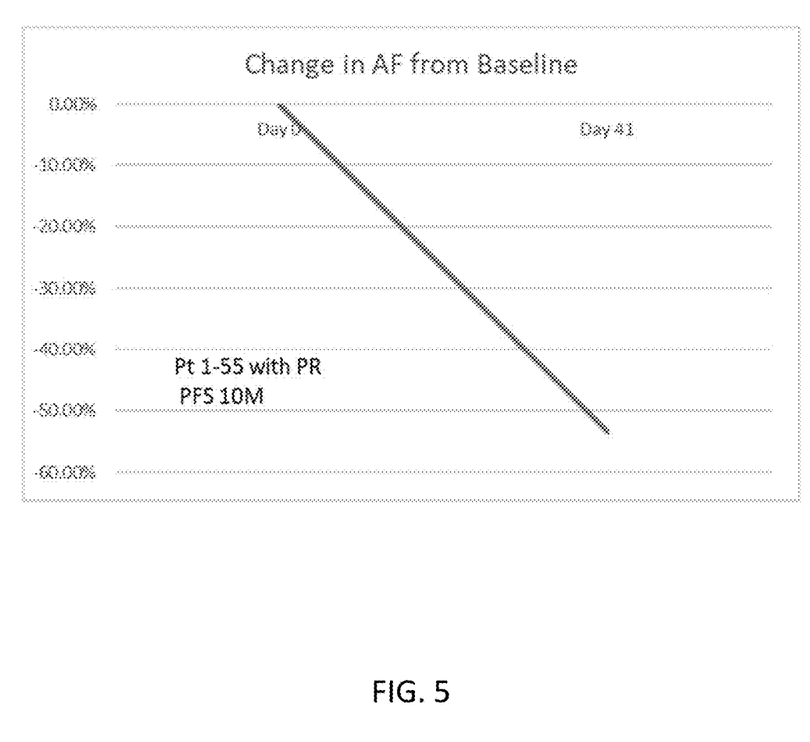
FIG. 5 shows the mutant allele frequencies monitored throughout treatment in a patient who demonstrated a clinical partial response while on therapy with nivolumab.

In contrast, a patient treated with nivolumab who demonstrated an approximately 2× reduction in the allele frequency of a TP53 transversion by day 41 of initiating therapy demonstrated a clinical partial response with a progression-free survival interval of 10 months (FIG. 5).

Example 4

Sequencing Method

Patients identified with stage IIIB/IV NSCLC are consented for blood collection for analysis prior to receipt of immunotherapy with PD-1/PD-L1 targeting therapy and when feasible, serial samples are collected prior to receiving additional doses at 2-3 week intervals.

Whole blood is collected into Streck Blood collection tubes (Streck BCT). Upon collection, the Streck BCTs are gently inverted 8-10 times before being shipped immediately. Within 7 days they are centrifuged at 1600×g for 10 minutes at room temperature, plasma is removed, transferred to a new tube and then a 2nd centrifugation step is performed at 20,000×g for 10 minutes to pellet any remaining cellular debris before transferring the plasma to a new tube. Upon completion of processing all cfDNA samples are frozen at −80° C. until ready for analysis.

Cell free DNA is extracted from plasma using the QIAamp Circulating Nucleic Acid kit (Qiagen). Digital PCR is then performed using the BioRad QX200 and an assay targeting a 108 bp region of the ribonuclease P/MRP subunit p30 (RPP30) gene.

Between 2,000 and 16,000 amplifiable copies (as measured by digital PCR) are then used to setup a sequencing library. PCR Primers targeting AKT1, ALK, BRAF, CCND1, CDKN2A, CTNNB1, EGFR, ERBB2, ESR1, FGFR1, FGFR2, FGFR3, GATA3, GNA11, GNAQ, GNAS, HRAS, IDH1, IDH2, KIT, KRAS, MAP2K1, MET, MYC, NFE2L2, NRAS, NTRK1, NTRK3, PDGFRA, PIK3CA, PPP2R1A, PTEN, ROS1, STK11, TP53 and U2AF1 are multiplexed together. These are used to amplify these 36 genes from the cell free DNA. Following PCR, the products are cleaned up using SPRIselect reagent (Beckman Coulter B23319) using the manufacturers protocol. DNA is then eluted in 18 uL. A second round of PCR is performed targeting sequences added during the first PCR. Each primer pair contains a unique barcode combination to enable subsequent sample demultiplexing.

The PCR product was cleaned up once using SPRIselect reagent (Beckman Coulter B23319) using the manufacturers protocol. Indexed samples are pooled into a tube containing 10 uL 10 mM Tris-HCl pH 8. Samples are then size selected for 195-350 bp using a 2% Agarose Dye Free cassette and marker L on the Pippin Prep (Sage Science), following the manufacturer's instructions. Size selected DNA is quantified by Qubit, following the manufacturer's instructions. Quantified libraries are sequenced on the NextSeqS00 Illumina platform (300 cycle PE) with 5% PhiX to monitor sequencing performance and data analysis is performed.

Sequencing files are analyzed using the Inivata Somatic Mutation Analysis (ISoMA) pipeline to identify SNVs, CNVs and indels. In the ISoMA pipeline a minimum Phred quality score of 30 for each base is required for inclusion in the analytics. For SNV and indel analysis, a background model is first established using samples from presumed healthy donors for each position/base pair change covered by our panel. The final determination of an SNV call integrates the data across multiple replicates for each sample in comparison with this background within a maximum likelihood framework. The same statistical principle is used for indels using samples from the same analytical batch in order to enable appropriate background calibration. The minimum depth at which any SNV or indel would be called is 1000×.

Mutations are classified as a transition mutation if they are a C>T, T>C, A>G or G>A change. They are classified as a transversion if they are an A>C, C>A, G>T, T>G, A>T, T>A, G>C or C>G. Patients with actionable EGFR or BRAF mutations, or either ALK or ROS1 fusions are recommended targeted therapy and classified as Low. Patients with no ctDNA detected or predicted loss of function mutations in PTEN or STK11 detected are classified as Low. Of the remaining patients, those identified with the presence of transversions in the target list of genes (particularly TP53, KRAS, CDKN2A, and NFE2L2) are classified as High. The remaining patients with just transition mutations are classified as Low.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications (e.g. ctDNA analysis) those skilled in the art will recognize that its usefulness is not limited thereto and that the present invention can be beneficially utilized in any number of environments and implementations where it is desirable to examine cfDNA. Accordingly, the claims set forth below should be construed in view of the full breadth and spirit of the invention as disclosed herein.

What is claimed is:

1. A method for treating a patient suffering from non-small cell lung cancer with an immune checkpoint inhibitor, wherein the method comprises:
    (a) obtaining or having obtained a sample of blood from the patient;
    (b) performing or having performed a sequencing assay on TP53, KRAS, PTEN, STK11, EGFR, BRAF, ALK and ROS1 on cell-free DNA (cfDNA) from the blood sample;
    (c) identifying the patient as having one or more nucleotide transversions in the coding sequences of either TP53 or KRAS or in TP53 and KRAS, no predicted loss of function mutations in PTEN or STK11, no activating mutations in EGFR or BRAF and no rearrangements in ALK or ROS1; and
    (d) administering an effective amount of the immune checkpoint inhibitor to the patient identified in step (c).

2. The method of claim 1, wherein the sequencing assay is done by:
    (i) amplifying the coding sequences of the genes in a multiplex PCR reaction in which at least 10 amplicons are amplified; and
    (ii) sequencing the amplicons.

3. The method of claim 1, wherein the sequencing assay comprises determining if there are any A to C transversions, determining if there are any C to A transversions, determining if there are any G to T transversions, determining if there are any T to G transversions, determining if there are any A to T transversions, determining if there are any T to A transversions, determining if there are any G to C transversions and determining if there are any C to G transversions in TP53 and KRAS.

4. The method of claim 1, wherein the immune checkpoint inhibitor is an antibody.

5. The method of claim 4, wherein the antibody is an anti-PD-1 antibody.

6. The method of claim 4, wherein the antibody is an anti-PD-L1 antibody.

7. The method of claim 1, comprising:
    receiving a report indicating whether there are any nucleotides transversion in TP53 or KRAS, whether there are any predicted loss of function mutations in PTEN or STK11, whether there are any activating mutations in EGFR or BRAF, and whether there are any rearrangements in ALK or ROS1.

8. The method of claim 7, wherein the report comprises a score indicating the likelihood of whether the patient will respond to the L1 immune checkpoint inhibitor.

9. The method of claim 7, wherein the report comprises a list of treatment options for PD-1/PD-L1 immune checkpoint inhibition.

10. The method of claim 1, wherein the activating mutations in EGFR and BRAF comprise: G719X, exon19 deletions, V765A, T783A, V774A, S784P, L858R and L861X in EGFR and V600E; L601G; K601E; L597V/Q/R and G469V/S/R/E/A in BRAF.

11. The method of claim 1, wherein the rearrangements in ALK and ROS1 comprise EML4-ALK, TFG-ALK, KIF5B-ALK, CD74-ROS1, SLC34A2-ROS1, SDC4-ROS1 and EZR-ROS1 fusions.

* * * * *